United States Patent [19]

Shroot et al.

[11] Patent Number: 5,602,104
[45] Date of Patent: Feb. 11, 1997

[54] POLYCYCLIC AROMATIC DERIVATIVES, PROCESS FOR PREPARING THE SAME AND PHARMACEUTICAL AND COSMETIC COMPOSITIONS CONTAINING THE SAME

[75] Inventors: Braham Shroot, Antibes; Jacques Eustache, Grasse; Oliver Watts, Cagnes S/Mer; Jean-Michel Bernardon, Nice; Philippe Nedoncelle, Grasse, all of France

[73] Assignee: Centre International de Recherches Dermatologiques Galderma (Cird Galderma), Valbonne, France

[21] Appl. No.: 421,235

[22] Filed: Apr. 13, 1995

Related U.S. Application Data

[62] Division of Ser. No. 859,046, Mar. 27, 1992, Pat. No. 5,434,180, which is a division of Ser. No. 580,916, Sep. 12, 1990, Pat. No. 5,124,473, which is a continuation-in-part of Ser. No. 887,618, Jul. 21, 1986, abandoned.

[30] Foreign Application Priority Data

Jul. 25, 1985 [LU] Luxembourg ................. 86022

[51] Int. Cl.$^6$ .................. A01N 43/08; C07D 307/02; C07D 333/16
[52] U.S. Cl. .................. 514/25; 514/242; 514/436; 514/444; 514/448; 514/461; 514/471; 514/473; 536/4.1; 536/17.2; 536/18.2; 536/18.5; 536/55.2; 536/55.3; 549/59; 549/71; 549/72; 549/75; 549/77; 549/78; 549/385; 549/472; 549/496; 549/497; 549/499; 549/501
[58] Field of Search .................. 549/385, 71, 78, 549/497, 499, 501, 72, 75, 77, 472; 536/4.1, 17.2, 18.2, 18.5, 55.2, 55.3; 514/24, 25, 42, 438, 444, 461, 471, 473, 448

[56] References Cited

U.S. PATENT DOCUMENTS

| | | | |
|---|---|---|---|
| 2,153,135 | 4/1939 | Dickey et al. .................. | 28/1 |
| 2,532,515 | 12/1950 | Pines et al. .................. | 260/348 |
| 3,940,502 | 2/1976 | Winter et al. .................. | 426/536 |
| 4,578,522 | 3/1986 | Eaddy, III .................. | 568/425 |

OTHER PUBLICATIONS

Chemical Abstract vol. 86 No. 6381, Liebscher et al, "Heterocyclic dyes and intermediates" (1976).
Chebaane, Societe Chimique de France, BCCFAS (1122) pp. 2521–2526, Jan. 12, 1975.
Hawley's Condensed Chemical Dictionary, 11 Ed., 1989, pp. 100.

Primary Examiner—Bernard Dentz
Assistant Examiner—Raymond Covington
Attorney, Agent, or Firm—Cushman Darby & Cushman Intellectual Property Group of Pillsbury Madison & Sutro, LLP

[57] ABSTRACT

A polycyclic aromatic compound having the formula

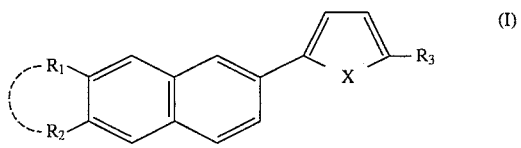

(I)

and its salts have useful therapeutic and cosmetic action particularly in psoriasis. In the formula, X represents —CH=CH—, O or S, $R_1$ represents hydrogen, branched alkyl having 3–15 carbon atoms, alkoxy having 1–6 carbon atoms or 1-adamantyl, $R_2$ represents hydroxy, hydrogen, linear or branched alkyl having 1–15 carbon atoms Or alkoxy having 1–6 carbon atoms, with the proviso that $R_1$ and $R_2$ are not simultaneously hydrogen, or $R_1$ and $R_2$ together with the adjacent carbon atoms of the naphthalene ring form a 5 or 6 chain ring optionally substituted by at least one lower alkyl radical, or interrupted by an oxygen atom, $R_3$ represents —CH$_2$OH or —COR$_4$, or —CH$_3$ when $R_1$ and $R_2$ taken together form a 5 or 6 chain ring, $R_4$ represents —OR$_5$ or

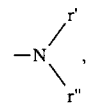

$R_5$ represents hydrogen, alkyl having 1–20 carbon atoms, monohydroxyalkyl, polyhydroxyalkyl, aryl or aralkyl optionally substituted, or the residue of a sugar or the radical

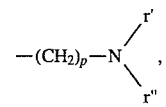

p is 1, 2 or 3, r' and r" represent hydrogen, lower alkyl, monohydroxyalkyl, polyhydroxyalkyl, aryl optionally substituted or the residue of an amino acid or the residue of an amino sugar, or taken together form a heterocycle.

15 Claims, No Drawings

POLYCYCLIC AROMATIC DERIVATIVES, PROCESS FOR PREPARING THE SAME AND PHARMACEUTICAL AND COSMETIC COMPOSITIONS CONTAINING THE SAME

This is a division of application Ser. No. 07/859,046, filed Mar. 27, 1992, now U.S. Pat. No 5,434,180 which is a division of application Ser. No. 07/580,916, filed Sep. 12, 1990 now U.S. Pat. No. 5,124,475 which is a continuation-in-part of application Ser. No. 06/887,618, filed Jul. 21, 1986, now abandoned The present invention relates to new polycyclic aromatic derivatives, to processes for their preparation and to their use in therapeutic and cosmetic formulations.

These polycyclic aromatic derivatives are usefully employed in the systemic and topical treatment of dermatologic ailments linked to a keratinization disorder (differentiation-proliferation) and dermatologic ailments, or others, with inflammatory and/or immuno-allergic components. They are also useful in the treatment of degeneratring maladies of the conjunctive tissue and they exhibit an antitumoral activity. Besides, these derivatives can be used in the treatment of atopy, be it cutaneous or respiratory, and in the treatment of rheumatoid psoriasis.

The compounds of the present invention are also useful in the field of ophthalmology and principally in the treatment of corneopathy.

The polycyclic aromatic derivatives according to the present invention can be represented by the following general formula

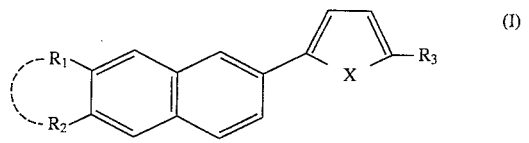

wherein

X represents —CH══CH—, O or S, $R_1$ represents hydrogen, branched alkyl having 3–15 carbon atoms, alkoxy having 1–6 carbon atoms or 1-adamantyl, $R_2$ represents hydrogen, hydroxy, linear or branched alkyl having 1–15 carbon atoms or alkoxy having 1–6 carbon atoms, with the proviso that $R_1$ and $R_2$ are not simultaneously hydrogen, or $R_1$ and $R_2$ together with the adjacent carbon atoms of the naphthalenic ring, form a ring having 5 or 6 chains, optionally substituted by at least one lower alkyl radical, or interrupted by an oxygen atom, $R_3$ represents —$CH_2OH$ or —$COR_4$, or even —$CH_3$ when $R_1$ and $R_2$ taken together form a ring having 5 or 6 chains, $R_4$ represents —$OR_5$ or

$R_5$ represents hydrogen, alkyl having 1–20 carbon atoms, monohydroxyalkyl, polyhydroxyalkyl, aryl or aralkyl, optionally substituted, or the residue of a sugar, or even the radical,

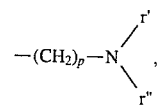

wherein p is 1, 2 or 3, r' and r" represent hydrogen, lower alkyl, monohydroxyalkyl, polyhydroxyalkyl, aryl optionally substituted or the residue of amino acid or an amino sugar or when taken together they form a heterocycle, and the salts of said polycyclic aromatic derivatives of Formula I.

By alkyl radical having 1–20 carbon atoms is meant, principally, methyl, ethyl, propyl, 2-ethylhexyl, octyl, dodecyl, hexadecyl, and octadecyl.

By lower alkyl is meant a radical having 1–4 carbon atoms, principally, methyl, ethyl, isopropyl, butyl and tert.butyl.

By monohydroxyalkyl is meant a radical containing 2–3 carbon atoms such as 2-hydroxyethyl or 2-hydroxypropyl.

By polyhydroxyalkyl is meant a radical containing 3–6 carbon atoms and from 2–5 hydroxy groups such as 2,3-dihydroxypropyl, 2,3,4-trihydroxybutyl, 2,3,4,5-tetrahydroxy pentyl or the residue of pentaerythritol.

By the residue of a sugar is meant the residue derived, for example, from glucose, mannose or from erythrose or from galactose.

Representative residues of amino sugars include those derived from glucosamine, galactosamine or mannosamine.

Representative alkoxy-radicals having from 1–6 carbon atoms include methoxy, isopropoxy and tert.butoxy.

When the radicals r' and r" taken together form a heterocycle, the heterocycle is, preferably, a piperidino, piperazino, morpholino or pyrrolidino radical.

When the compounds according to the present invention are provided in the form of salts, they can be salts of an alkali or alkaline earth metal or even of zinc, or they can be salts of an organic amine when they have at least one free acid function ($R_3$=COOH), or they can be salts of a mineral or organic acid, principally the hydrochloride, hydrobromide or citrate when they have at least one amine function.

Particularly preferred compounds of Formula I according to the present invention, are those wherein $R_3$=COOR$_5$ and more particularly those corresponding to formulae A,B,C and D as follows:

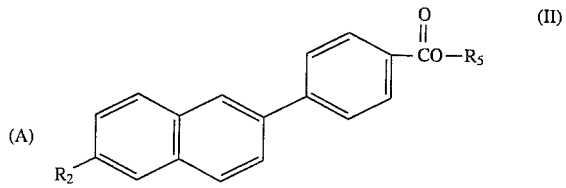

wherein $R_5$ represents hydrogen or alkyl and $R_2$ represents branched lower alkyl;

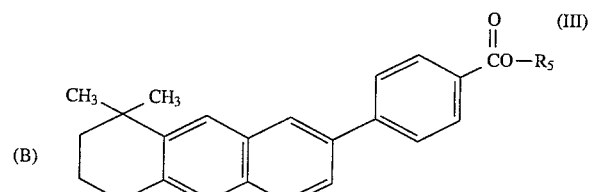

wherein $R_5$ represents hydrogen or alkyl;

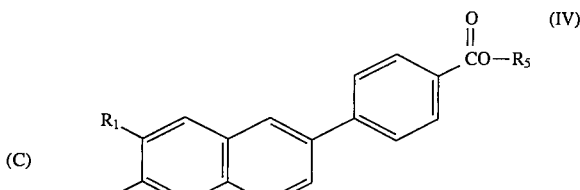

wherein $R_1$ represents tert.butyl or 1-adamantyl, and $R_5$ represents hydrogen or alkyl;

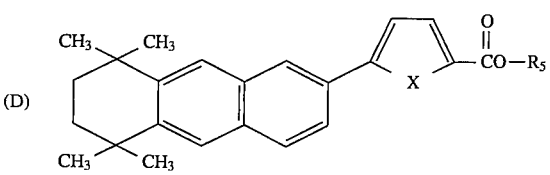

wherein

X represents O or S, and $R_5$ represents hydrogen or alkyl.

Certain compounds similar to those of formula (A) are disclosed in U.S. Pat. No. 4,578,522 where they are noted as being useful for controlling blood lipids. This difference in utility is thought to be at least in part a function of the position of the carboxyl group in the respective molecules.

In this U.S. patent, the carboxyl group is in the ortho position instead of the para position of formula A above. The importance of the para position for retinoid mimicry is noted by SPORN et al in "The Retinoids" Vol 1, especially chapter 3, page 237 and by STRICKLAND et al in Cancer research 43, 5268–5272 (1983) especially page 5271. Both these documents are incorporated herein by reference.

Representative compounds of Formula I include principally:

p-(6-tert.butyl-2-naphthyl) benzoic acid, p-(5,6,7,8-tetrahydro-5,5,8,8-tetramethyl-2-anthracenyl) benzoic acid and its ethyl, 2hydroxyethyl and 2,3-dihydroxyprophyl esters, the diethylamide of p-(6-tert.butyl-2-naphthyl) benzoic acid, the monoethylamide of p-(5,6,7,8-tetrahydro-5,5,8,8-tetramethyl-2-anthracenyl) benzoic acid, p-(6-methoxy-2-naphthyl) benzoic acid and its methyl ester, p-(5,6,7,8-tetrahydro-5,5,8,8-tetramethyl-2-anthracenyl) benzyl alcohol, 2-(p-methylphenyl)-5,6,7,8-tetrahydro5,5,8,8-tetramethyl anthracene, the p-hydroxyphenyl amide of p-(5,6,7,8-tetrahydro-5,8,8-tetramethyl-2-anthracenyl) benzoic acid, p-[7-(1-adamantyl)-6-methoxy-2-naphthyl]-benzoic acid and its methyl ester, p-(7-tert.butyl-6-methoxy-2naphthyl) benzoic acid and its methyl ester, p-[7-(1-adamantyl)-6-hydroxy-2-naphthyl]benzoic acid and its methyl ester, 5-(5,6,7,8-tetrahydro-5,5,8,8-tetramethyl-2-anthracenyl)-2-furan carboxylic acid and its methyl ester, 5-(5,6,7,8-tetrahydro-5,5,8,8-tetramethyl-2-anthracenyl)-2-thiophene carboxylic acid and its methyl ester, the ethylamide of 5-(5,6,7,8-tetrahydro-5,5,8,8-tetramethyl-2-anthracenyl)-2-furan carboxylic acid, the morpholide of 5-(5,6,7,8-tetrahydro-5,5,8,8-tetramethyl-2-anthracenyl)-2-furan carboxylic acid, 5-(5,6,7,8-tetrahydro-5,5,8,8-tetramethyl-2-anthracenyl)-2-furan carboxylate of 2hydroxyethyl, p-[3,4(2H)-dihydro-4,4-dimethyl-7-naphtho (2,3-b) pyrannyl] benzoic acid and its methyl ester, 2-(4-methylphenyl)-5,6,7,8-tetrahydro-5,5,8,8-tetramethyanthracene, Although various synthesis methods can be envisaged in the production of the compounds of Formula I, it is preferred to employ, in accordance with the present invention the method represented by the following reaction scheme:

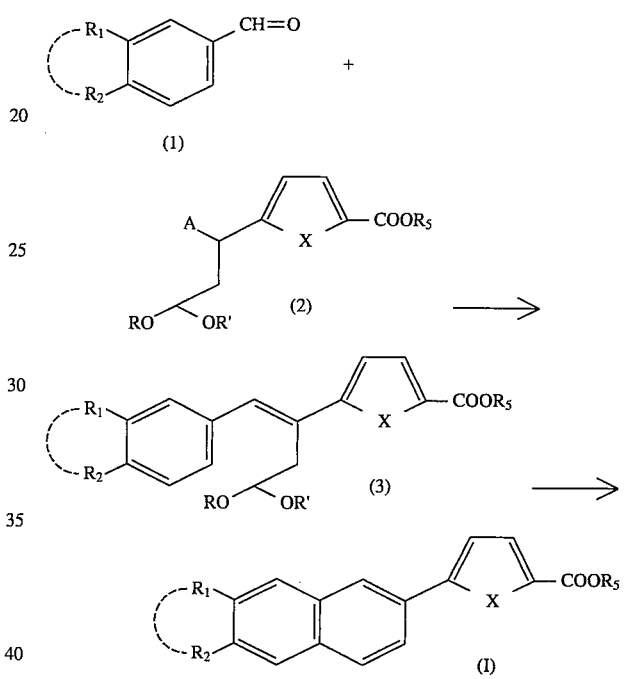

R and $R^1$ represent an alkyl radical or taken together form a dioxane or dioxolane ring.

According to this method, a coupling reaction of the Wittig or Wittig-Horner type initially is effected between an aromatic aldehyde (1) and a pentavalent phosphorus derivative (2).

In the derivative (2) the radical A can represent either a triaryl phosphonium group of the formula:

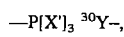

wherein X' is aryl and Y is an anion of an organic or inorganic acid, or a dialkoxyphosphinyl group of the formula:

wherein Z is alkoxy, preferably, —$OC_2H_5$.

When A represents —$P[X']_3{}^+Y^-$, the coupling reaction is carried out in the presence of an alkali metal alcoholate, such as sodium methylate, or in the presence of an alkylene oxide optionally substituted by an alkyl group, in a solvent such as methylene chloride or dimethylformamide. The reaction temperature ranges between 0° C. and the boiling temperature of the reaction mixture.

When A represents

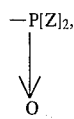

the condensation is carried out in the presence of a base and, preferably, in the presence of an inert organic solvent, for example, by means of sodium hydride or lithium dialkylamide in benzene, toluene, dimethylformamide (in the case of sodium hydride), tetrahydrofuran, dioxane or 1, 2-dimethoxyethane, or also by means of an alcoholate, for example, by means of sodium methylate in methanol or of potassium tert.butylate in THF, at a temperature between −80° C. and the boiling point of the reaction mixture. The condensation can also be carried out by using a mineral base such as KOH or NaOH, in an organic solvent such as tetrahydrofuran or under phase transfer conditions.

A ring ether, capable of complexing the metallic cation contained in the base, can be added to the reaction mixture so as to improve its strength.

The intermediate compound of formula (3) is generally obtained in the form of a mixture of transisomers (E) and cis isomers (Z) that can be separated by chromatography although the mixture of isomers can be used as such for the following step.

The cyclization-aromatization reaction is carried out in a chlorinated solvent such as dichloromethane or chloroform in the presence of, as a catalyst, a strong acid such as sulfuric acid or p-toluene sulfonic acid or a silylic ester of a strong acid such as, for example, the trifluoromethane sulfonate of trimethylsilyl.

When isomer (Z) of the compound of formula (3) or a mixture of (E)–(Z) isomers is employed the cyclization-aromatization reaction must be conducted under UV radiation in order to isomerize the isomer (Z) into its isomer (E).

In effect, under the reaction conditions, the isomers (Z) do not lead to the expected compounds of Formula I.

This cyclization-aromatization reaction is preferably carried out at ambient temperature.

The aromatic aldehydes of formula (1) are either available commercially, or easily accessible by known synthesis methods.

The preparation of the pentavalent phosphorus derivative of formula (2) can be carried out in accordance with the following reaction scheme:

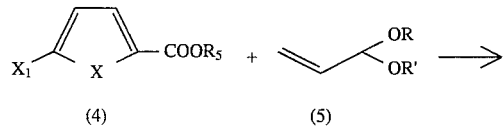

$X_1 = Br$ ou $Cl$

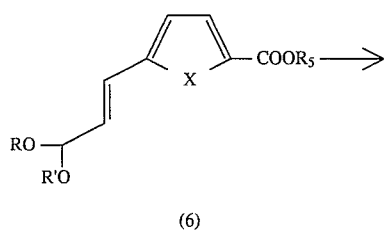

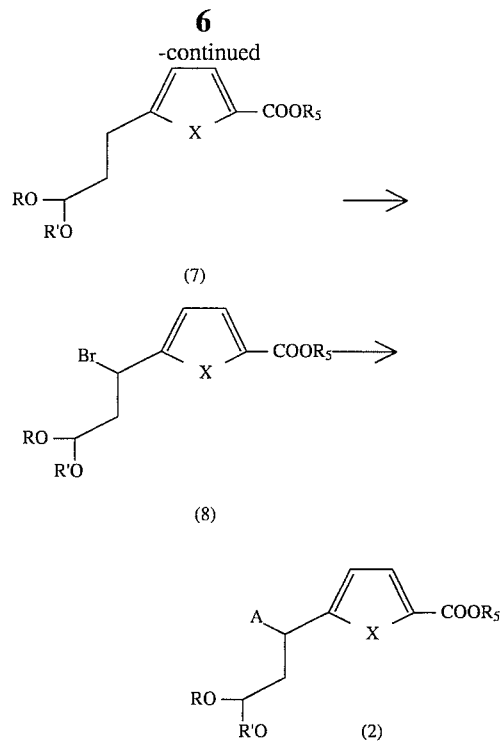

In accordance with this method a coupling reaction is initially effected between an alkyl halogeno ester (4) and an acrolein dialkylacetal (5) in the presence of a palladium salt and a base such as triethylamine, di-isopropylamine, sodium bicarbonate or sodim carbonate, the temperature being preferably between 70° and 150° C. The intermediate compound (6) is then hydrogenated to the compound of formula (7), then brominated by n-bromosuccinimide in carbon-tetrachloride to provide the brominated compound (8). This latter compound is then transformed into the pentavalent phosphorus compound of formula (2) by, for example, the aid of an organic phosphite such as triethyl phosphite in accordance with the conditions of the Arbusov reaction.

When the compounds of Formula I, in accordance with the present invention, are mono-substituted naphthalenic derivatives, ($R_1$ or $R_2=C_1-C_{15}$ alkyl) and more particularly the compounds of Formula II, it is preferred to employ the process represented by the following reaction scheme:

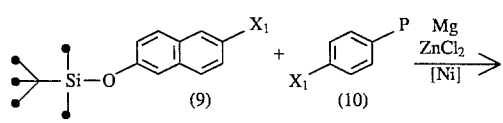

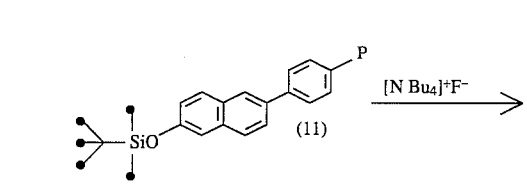

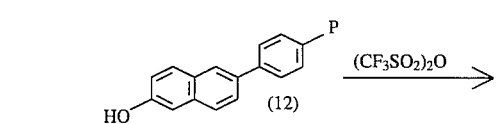

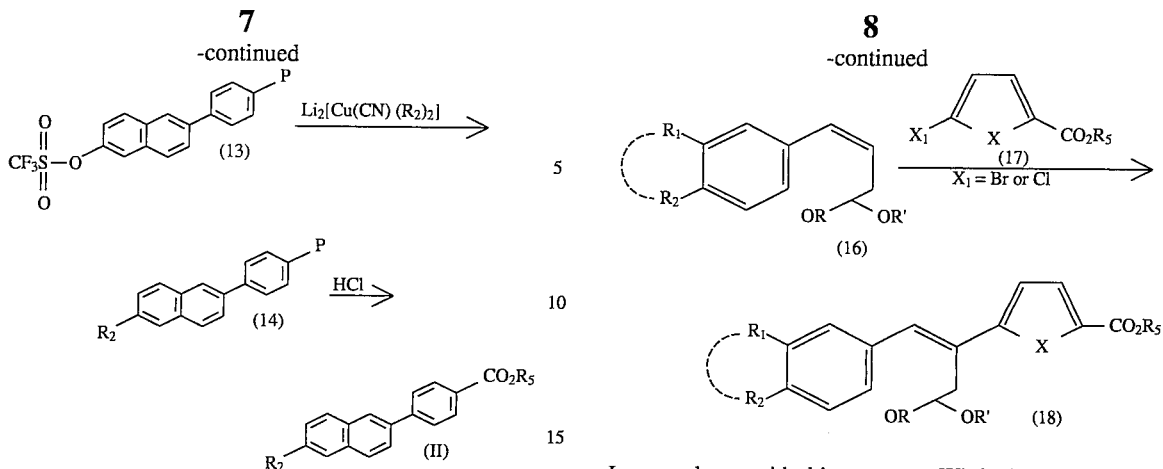

P= protective group able to generate the carbonyl function
X₁=Cl or Br.

In accordance with this process a coupling reaction is effected between a 6-halogeno-2-tert.butyl-dimethylsilyloxy naphthalene derivative (9) and a protected carbonyl derivative of a p-halogenobenzoic acid (10). In accordance with this process, the compound (10) is transformed into its magnesium, lithium or zinc form in accordance with methods known in the literature and coupled with the halogen derivative of naphthalene (9) by using, as the reaction catalyst, a transition metal or one of its complexes.

Representative particular catalysts include those derived from nickel or palladium and, in particular, compounds of Ni$_{II}$ (NiCl$_2$) with various phosphines, in particular diphenyl phosphinoethane.

The coupling reaction is generally effected at a temperature between −20 and +30° C. in an anhydrous solvent such as for example. dimethylformamide or tetrahydrofuran.

Various protective groups can be used to generate the carbonyl function of the p-halogenobenzoic acid. However, in accordance with the present invention an oxazolinyl group is preferably employed.

The benzonaphthalenic derivative of formula (11) is then treated with tetramethylammonium fluoride in tetrahydrofuran so as to obtain the naphthol derivative of formula (12). This latter derivative is then transformed into the trifluoromethanesulfonate derivative of formula (13) which, on treatment with an appropriate organocupric derivative, provides, in accordance with the method described by J.E. McMurray et al (Tetrahedron Letters 24, p. 2723, 1983), the naphthalene derivative of formula (14) substituted in the 6 portion by an alkyl radical. On removal of the protective group using HCl in an aqueous solution, compounds of Formula II are obtained wherein R$_5$=H.

To obtain the compounds of Formula I the process represented by the following reaction scheme can also be employed:

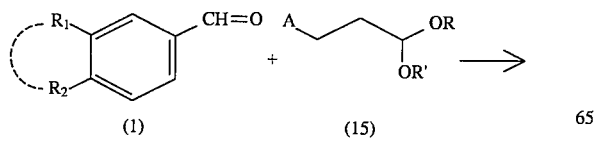

In accordance with this process a Wittig-Horner reaction is effected between an aromatic aldehyde (1) and a pentavalent phosphorus derivative (15) in which A has the same meanings as those given for Scheme A above, the reaction conditions also being the same. The resulting intermediate compound (16) is then treated with a heterocyclic halogenoester (17) in accordance with the Heck reaction so as to provide compound (18) which is then cyclized.

The coupling reaction between the aromatic aldehyde (1) and the pentavalent phosphorus derivative (15) is carried out, preferably, by the Wittig reaction (A=—P[∅]$_3$$^+$Br$^-$) using preferably as the base, potassium tert.butylate in THF. This provides the stereospecific production of compound (16) in its Z form. The use of lithium bases, such as lithium di-isopropylamide, leads to E+Z mixtures of the intemrediate (16). The Heck reaction is effected, preferably, between 120° and 220° C. (under nitrogen) and the reaction is generally carried out in the absence of a solvent. Amines having a high boiling point, for exajple diazabicycloundecene (DBU) can be used as bases but the best results are obtained using sodium carbonate as finely divided potassium, with the catalyst used being palladium (II) acetate in the presence of triphenylphosphine.

Starting with esters and acids obtained above it is possible to produce, in accordance with known-procedures compounds of Formula I wherein R$_3$ has any one of the other meanings given above.

The present invention also relates to the intermediate synthesis compounds represented by the following formula

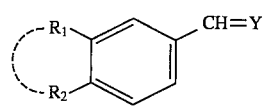

wherein

R$_1$ and R$_2$ have the same meanings given above for Formula I, and

Y represents ═O or

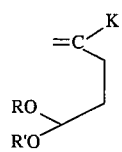

wherein K represents hydrogen or

wherein

X and $R_5$ have the same meanings as those given for Formula I, and

R and R' represent alkyl or, taken together, form a dioxane or dioxolane ring.

The present invention further relates to a medicine comprising the compounds of Formula I as defined above.

These compounds exhibit excellent activity in the inhibition test of ornithine decarboxylase in nude rats after induction, by "tape stripping". This test is recognized as a measure of the activity of retinoids of cellular proliferation phenomena.

These compounds are particularly appropriate for treating dermatologic ailments linked to a keratinization disorder (differentiation-proliferation) as well as dermatologic diseases, or others, having an inflammatory and/or immunoallergic component principally:

acnes vulgaris, comedons or-polymorphs, solar senile acne and medicinal or professional ache, extensive and/or severe forms of psoriasis, and other keratinization disorders, and principally ichtysoses and ichtysosis-like conditions, Darier malady, palmo-plantar keratodermies, leucoplasies and leucoplasi-like states, lichen plan all malignant or benign dermatologic proliferations, severe or extensive.

They are also active in the treatment of tumors, of rheumatoid psoriasis, cutaneous or respiratory atrophies as well as in certain ophthalomogic problems relating to corneopathies.

The present invention also relates to a medicinal composition containing at least one compound of Formula I, such as defined above, or one of its salts, at a concentration, preferably between 0.00001 and 5 percent by weight relative to the total weight of the composition.

The present invention thus relates to a new medicinal composition intended principally for the treatment of the above mentioned disorders, comprising in a pharmaceutically acceptable support, at least one compound of Formula I and/or one of its salts.

The compounds in accordance with the present invention exhibit, relative to known retinoids, better stability to light and oxygen, this being essentially due to the fact that they have no easily Isomerizable or oxidizable double bonds.

The compounds according to the present invention are generally administered at a daily dosage of about 0.01 μg/kg to 0.1 mg/kg of body weight.

As the vehicle or carrier for these compositions, any conventional vehicle can be employed, the active compound being found either in the dissolved state, or in the dispersed state in said vehicle.

The administration of the compounds of the present invention can be effected enterally, parenterally, topically or ocularly. When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotions, gels, sprays or suspensions.

These compositions for topical administration can be provided either under anhydrous form or in aqueous form according to clinical indications.

When administered ocularly, the composition is provided principally in the-form of an eyewash.

The compounds of Formula I, according to the present invention, are also useful in the cosmetic field, in particular, in body and hair hygiene compositions and principally for the treatment of skin having a tendency to age, to improve the growth of hair, to combat hair loss, to combat against an oily appearance of the skin or hair, in the protection against the harmful effects of the sun or in the treatment of physiologically dry skin.

The present invention thus relates to a cosmetic composition containing, in a cosmetically acceptable vehicle, at least one compound of Formula I or one of its salts, this composition being provided principally in the form of a lotion, gel, soap or shampoo.

The concentration of the compound of Formula I in these cosmetic compositions is between 0.00001 and 2 percent by weight and, preferably, between 0.00001 and 1 weight percent based on the total weight of the composition.

The medicinal and cosmetic compositions according to the invention can contain inert or even pharmacodynamic or cosmetically active additives and principally: hydrating agents such as thiamorpholinone and its derivatives or urea; antiseborrheic or anti-ache agents, such as S-carboxymethylcysteine, S-benzyl-cysteamine, their salts and their. derivatives, tioxolone or benzoylperoxide; antibiotics such as erythromycin and its esters, neomycin or tetracyclines; agents promoting the growth of hair such as "Minoxidil" (2,4-diamino-6-piperidino-pyrimidine-3-oxide) and its derivatives,-Diazoxide (7-chloro-3-methyl-1,2,4 benzothiadiazine 1,1-dioxide) and Phenytoin (5,5-diphenylimidazolidine-2,4 dione); steroidal and non-steroidal anti-inflammatory agents; carotenoids and, principally, β-carotene; antipsoristic agents such as anthralin and its derivatives and 5,8,11,14-eicosatetraynoic and 5,8,11-eicosatriynoic acids.

The compositions according to the present invention can also contain flavor improving agents, preservatives, stabilizers, humidity regulating agents, pH regulating agents, osmotic pressure modifying agents, emulsifiers, UV-A and UV-B filters, anti-oxidants such as α-tocopherol, butylhydroxyanisole or butylhydroxytoluene.

The following non-limiting examples illustrate the preparation of the active compounds of Formula I in accordance with the invention as well as compositions containing these compounds.

EXAMPLE I

Preparation of p-(6-tert.butyl-2- naphthyl) benzoic acid (a) 6-bromo-2-tert.butyl dimethylsilyloxy naphthene The following are dissolved in 50 ml of dimethylformamide: 10 g (45 mmoles of 6-bromo-2naphthol, 5.65 g(55 mmoles) of triethylamine and 0.12 g (1 mmole) of 4-dimethylamino pyridine.

7.55 g (50 mmoles) of tert.butyl dimethylsilyl-chloride are slowly added and the resulting solution is stirred for three hours at ambient temperature. The resulting mixture is poured over 200 ml of water, then acidified with concentrated HCl until a pH of about 1. The solution is extracted with ether (4×100 ml). The etherified solution is then washed with water, dried over anhydrous sodium sulfate and the solvent evaporated.

There is thus obtained a pale yellow oil which is purified, by elution with heptane, on a short silica column. After concentration of the solvent, a colorless oil which crystallizes is obtained. After drying, 13.2 g (87% yield) of the expected product is obtained. Melting point: 60°–62° C.

(b) 6-[p-(4,4-dimethyl-2-oxazolinyl)-phenyl]-2-naphthol 100 ml of anhydrous THF are added to a mixture of 15.3 g (60 mmoles) of p-(4,4-dimethyl-2-oxazolinyl)-bromobenzene, prepared in accordance with the method of A. Meyers et al, JOC, 29, 2787 (1974), and 1.75 g.(70 m. at-g) of magnesium. The reaction starts spontaneously and the reaction mixture is heated at reflux for 3 hours. After cooling, 8.16 g (60 moles) of anhydrous zinc chloride are added and the resulting mixture is stirred for 1 hour at ambient temperature. To the resulting white suspension 9.5 g (28 moles) of the compound obtained in part (a) above and 0.32 g (0.6 mmole) of $NiCl_2$/diphenylphosphinoethane are added. The mixture is stirred for an additional 3 hours. The reaction is stopped by the addition of a 2M aqueous solution of ammonium chloride. The reaction medium is then extracted with dichloromethane and the organic phase is washed with water, then dried over magnesium sulfate. After evaporation of the solvent an orange oil is obtained which is purified by passage through a short silica column, using, as the eluant, dichloromethane. After concentration of the elution solvent, 2-tert.butyldimethylsilyloxy 6[p-(4,4-dimethyl-2-oxazolinyl)-phenyl]naphthalene in the form of a white solid is obtained. This solid is dissolved in 50 ml of tetrahydrofuran and treated with 35 ml of a molar solution of tetrabutylammoniumfluoride in tetrahydrofuran. The reaction mixture is stirred at ambient temperature for 3 hours, then poured into water and extracted with dichloromethane. The organic phase, after having been washed with water, is dried over anhydrous magnesium sulfate and concentrated. An orange oil is obtained which is purified by elution through a short silica column, using, as the eluant, a 99/1 mixture of dichloromethane and methanol. The elution solvents are evaporated, yielding a pale yellow oil which crystallizes. After recrystallization in hot methanol, 5.5 g of crystals in the form of pale yellow needles are obtained (64% yield). Melting point: 221°–223° C.

(c) Trifluoromethane sulfonate of 6-[p-(4,4-dimethyl-2-oxazolinyl)-phenyl]2-naphthyl To a solution of 3.03 g (30 mmoles) of triethylamine, 0.025 g (0.2 mmole) of 4,4-dimethylaminopyridine and 5 g (15.8 mmoles) of the compound obtained in part (b) above, in 100 ml of dichloromethane at 0° C., 4.89 g (17.4 mmoles) of trifluoromethanesulfonic anhydride are added. The resulting mixture is stirred at ambient temperature for 2 hours and then poured into water, and acidified to pH 3 by the addition of concentrated HCl.

The acidified mixture is extracted with dichloromethane. The organic phase, after having been washed with water, is dried over anhydrous magnesium sulfate, and then concentrated, thereby providing an oily solid which is purified by elution through a short silica column using a 3/1 mixture of hexane/dichloromethane as the eluant.

After having evaporated the elution solvents under reduced pressure an oily solid is obtained which is recrystallized by hot cyclohexane, yielding 3 g of a white crystalline solid (42% yield). Melting point: 132°–135° C.

(d) 2-[p-(6-tert.butyl-2-naphthyl)-phenyl-4,4-dimethyl oxazoline

To a mixture of 0.9 g (10 mmoles) of copper cyanide in tetrahydrofuran cooled to −78° C., there are slowly added with stirring, 8.7 ml of a 2.3 molar (20 mmoles) hexane solution of tert.butyl lithium.

The mixture is left to stand until its temperature reaches 0° C. It is then cooled again to −78° C. whereupon 1.5 g (3.3 mmoles) of the compound obtained in part (c) above are added. The reaction mixture is again left to stand until its temperature reaches −20° C. at which point it is stirred for two additional hours. The reaction is stopped by the addition of a molar aqueous solution of ammonium chloride. The reaction mixture is then extractd with dichloromethane and the organic phase is washed with water, dried over magnesium sulfate and concentrated under reduced pressure.

A pale yellow solid is obtained which is then purified by preparative HPLC (ZORBAX SIL, diisopropyl ether/isooctane/triethylamine, 75/25/1), yielding 0.35 g (30% yield) of a pale yellow solid having a melting point of 154°–159° C.

(e) p-(6-tert.butyl-2-naphthyl) benzoic acid 0.3 g (0.8 mmole) of the compound obtained in part (d) above is heated to reflux in 20 ml of a 3M HCl acid solution for 3 hours. A white precipitate results which is then filtered and redissolved in 20 cc of methonalic NaOH at 20%. This mixture is heated at reflux for 30 minutes. The white precipitate that forms is filtered, washed with water and dried at 75° C. under a vacuum for 24 hours.

0.09 g (40% yield) of the expected acid having a melting point of 310°–315° C. is thus obtained.

EXAMPLE II

Preparation of the ethyl ester of
p-(5,6,7,8-tetrahydro-5,5,8,8-tetramethyl-2-anthracenyl) benzoic acid (a) Ethyl ester of p-(3,3-dimethoxypropyl) benzoic acid 83.58 g of ethyl p-bromobenzoate are dissolved in 100 ml of dioxane, to which are successively added 3.83 g of triphenylphosphine, 41.00 g of acrolein dimethylacetal, 100 g of potassium carbonate and 1.64 g of palladium (II) acetate.

The resulting mixture is heated to 110° C., while stirring for 16 hours and then filtered over kelite. The kelite filter is washed with 3×200 ml of ethyl ether and the wash medium is then dried and evaporated yielding 90.37 g of a yellow oil that is dissolved in 365 ml of methanol. 1.46 g of palladium on carbon (5%) are added and hydrogenation is carried out. When the absorption of the hydrogen is terminated, the catalyst is removed by filtration on kelite. After evaporation of the methanol, the residue is chromatgraphed (silica column, 30×10 cm, eluant: 50/50 mixture of dichloromethane and hexane), yielding, after evaporation of the solvents, 72.77 g (79% yield) of the ethyl ester of p-(3,3-dimethoxy propyl)-benzoic acid.

(b) Ethyl ester of p-(1-diethoxyphosphoryl-3,3-dimethoxypropyl)-benzoic acid 70.00 g of the product obtained in part (a) above are dissolved in 1000 ml of carbon tetrachloride. 1 g of benzoyl peroxide is added and then 49.38 g of N-bromo succinimide are added by fractions. The resulting mixture is heated at reflux for 45 minutes, and the succinimide that forms is removed by filtration on kelite. The solvent is evaporated and the resulting oil is dried at ambient temperature under a vacuum (1 mm Hg).

The oil thus produced is dissolved in 400 ml of trtethylphosphite, and heated to 160° C. for 18 hours. The triethylphosphite is evaporated at 120° C. under vacuum of a water-jet pump. The residues is deposited on a silica column (30×10 cm), then eluted with a 70/30 mixture of ethyl acetate and hexane, yielding 46.64 g (45% yield) of the ethyl ester of p-(1-diethoxyphosphoryl-3,3-dimethoxypropyl)-benzoic acid.

(c) Ethyl ester of p-[1-(2,2-dimethoxyethyl)-2-(5,6,7,8-tetrahydro-5,5,8,8-tetramethyl- 2-naphthyl)-vinyl ]benzoic acid 31.76 g of the phosphonate obtained above in part (b) are dissolved in 75 ml of tetrahydrofuran. This solution is then cooled to −78° C. and a solution of lithium diisopropyl amide, prepared starting with diisopropyl amine (12.5 ml) and n-butyllithium (1.6 ml in hexane) in 75 ml of tetrahydrofuran, are slowly added thereto.

To this resulting red solution there is added a solution of 5,6,7,8-tetrahydro-5,5,8,8-tetramethyl-2-naphthaldehyde (16.08 g) in 50 ml of tetrahydrofuran. This mixture is stirred initially for 90 minutes at −78° C. and then for 90 minutes at ambient temperature.

150 ml of water are then added and the mixture is extracted with ether (3×200 ml).

The organic phase is washed with a saturated solution of sodium chloride and dried over magnesium sulfate. The dried organic phase is filtered. The solvents are evaporated. The resulting residue is chromatographed on a silica column (30×10 cm) using, as the eluant, a 30/70 mixture of ethyl ether and hexane.

There are thus obtained successively:

(A) 8.02 g of ethyl p-[(E)[1–2,2-dimethoxyethyl)-2-(5,6,7,8-tetrahydro-5,5,8,8-tetramethyl-2-naphthyl)]-vinyl]- benzoate, having a melting point of 82° C. and (B) 8.24 g of ethyl p-[(Z)-[1-(2,2-dimethoxyethyl)-2-(5,6.,7,8-tetrahydro-5,5,8,8-tetramethyl-2-naphthyl)]-vinyl]benzoate.

The yield of A+B is 50%.

(d) Ethyl ester of p-(5,6,7,8-tetrahydro-5,5,8,8-tetramethyl-2-anthracenyl)-benzoic acid (i) Method I 7.02 g of the (E) isomer of the ester obtained in part (c) above are dissolved in 80 ml of dichloromethane. To this solution there are added 2 ml of the trimethylsilic ester of trifluoromethane sulfonic acid and the mixture is stirred for 15 minutes at ambient temperature. The dichloromethane is evaporated and the residue is introduced into the top of a short silica column (5×10 cm) and eluted with a 60:40 mixture of methylene chloride and heptane. An evaporation of the solvents, 5.65 g (94% yield) of the ethyl ester of p-(5,6,7,8-tetrahydro-5,5,8,8-tetramethyl-2-anthracenyl) benzoic acid having a melting point of 126° C. are obtained.

(ii) Method II 7.80 g of the (Z) isomer of the ester obtained in part (c) above are dissolved in 350 ml of dichloromethane. 1 ml of the trimethylsilic ester of trifluoromethane sulfonic acid is added and the reaction mixture is placed in a photochemical reactor. The reaction mixture is stirred for 3 hours, at ambient temperature, while it is irradiated (Hanovia average pressure lamp, without filter). The dichloromethane is evaporated and the deep green residue is deposited at the top of a silica column (30×8 cm) and eluted with a 40:60 mixture of dichloromethane and heptane. After evaporation of the solvents, 2.67 g (40% yield) of the ethyl ester of p-(5,6,7,8-tetrahydro-5,5,8,8- tetramethyl-2-anthracenyl)-benzoic acid are obtained.

EXAMPLE III p-(5,6,7,8-tetrahydro-5,5,8,8-tetramethyl-2-anthracenyl)-benzoic acid 7.32 g of the ester obtained in Example II(d) are suspended in 400ml. of ethanol 38 ml of 5N NaOH are added to this suspension which is then heated at 60° C. for 60 minutes. The ethanol is evaporated and the residue is taken up in water (500 ml) and acidified to pH 1 with 6N HCl. It is then extracted with ether (3×500 ml) and the organic phase is dried over $MgSO_4$. After filtration and evaporation of the solvents, 30 ml of the ethyl ester are added to the residue, yielding after stirring and filtration, 6.25 g (92% yield) of p-(5,6,7,8-tetrahydro-5,5,8,8-tetramethyl-2-anthracenyl)-benzoic acid having a melting point of 282° C.

EXAMPLE IV

Methyl ester of p-[7-(1-adamantyl)-6-methoxy-2-naphthyl]-benzoic acid (a) 3-(1-adamantyl)-4-methoxy benzaldehyde 11.09 g (37 mmoles) of 2-(1-adamantyl)-4bromo anisole dissolved in 85 ml of THF are slowly added to 1 g of magnesium and an iodine crystal. At the beginning of the addition, the reaction mixture is heated until the reaction begins, then the remainder of the solution is added in a manner to maintain a regular reflux. This reaction mixture is heated at reflux for 30 minutes after the end of the addition at which point 2.70 g (37 mmoles) of dry DMF are added. The reaction mixture is then stirred for 30 minutes without heating and then-poured into 300 ml of mixture of 2N aqueous HCl and dichloromethane.

The organic phase is decanted and the aqueous phase is extracted with dichloromethane. The organic extracts are combined, washed with a saturated solution of sodium bicarbonate, then with a saturated solution of sodium chloride, dried over magnesium sulfate, filtered and the solvents evaporated.

The resulting residue is purified by passage through a silica column (eluant: 60:40 mixture of dichloromethane and hexane). After evaporation of the solvents the expected aldehyde, 8.0 g (80% yield) in the form of a light yellow powder which melts at 180° C. is obtained.

(b) Methyl ester of p-[1-(2,2-dethoxyethyl)-2-[3-(1-adamantyl)-4-methoxyphenyl]-vinyl]-benzoic acid 11.42 g (30.51 moles) of the phosphonate obtained in EXAMPLE II(b) are dissolved in 50 ml of THF. This solution is then cooled to −78° C. and there is slowly added thereto a solution of lithium di-isopropylamide which was prepared in a conventional manner starting with 3.4 g (33.58 mmoles) of di-isopropylamine and 2.1 ml (33.56 mmole) of a solution of N-butyllithium (1.6M in hexane). The red-orange solution thus obtained is stirred for 30 minutes at −78° C. and a suspension of 3-(1-adamantyl)-4-methoxy-benzaldehyde obtained above in part (a) (7.5 g 27.74 moles) in 140 ml of THF is added in fractions thereto. This addition lasts for about 10 minutes. The reaction mixture is then stirred initially for 20 minutes at −78° C. and then for 2 hours at 25° C. The mixture is poured into water and extracted three times with 100ml ethylether. The organic phase is washed with a saturated solution of sodium chloride, dried over magnesium sulfate, filtered and the solvents evaporated. The residue in chromatographed on a silica column, as in Example II(c), yielding a mixture of two isomers, E and Z, of the methyl ester of p-[1-(2,2-dimethoxyethyl)-2-[3-(1-adamantyl)-4methoxyphenyl]-vinyl]benzoic acid (7.5 g, 53% yield) in the form of a partially crystallized light yellow oil. This mixture is used as such in the continuation of the synthesis.

(c) Methyl ester of p-[7-(1-adamantyl)-6-methoxy-2-naphthyl]-benzoic acid

To 6.65 g (13.55 mmole) of the mixture obtained above in part (b) in 400 ml of dichloromethane, there are added 2 ml of the trimethyl ester of trifluoromethyl sulfonic acid (TMSOTf). This mixture is irradiated with ultraviolet (UV) as in Example II(d), for 4 hours. The solvents are evaporated, then the reaction mixture is purified by passage through a silica column (eluant: 70:30 mixture of dichloromethane and hexane). The fractions containing the expected product are concentrated under a vacuum. The resulting residue is filtered, washed with 300 ml of cold hexane, then dried under a vacuum at ambient temperature, yielding 4.65 g (80% yield) of the expected product, in the form of a yellowish white solid which melts at 245° C.

EXAMPLE V p-[7-(1-adamantyl)-6-methoxy-2-naphthyl ]-benzoic acid 1.28 g, (3 mmoles) of the ester obtained in Example IV(c) are suspended in 60 ml of methanol. To the suspension are added 6 ml of 5N NaOH and the mixture is stirred while heating at reflux for 6 hours. 200 ml of methanol and 200 ml of water are then added and the resulting solution is concentrated in a manner to remove most of the methanol. 300 ml of ethylether and 200 ml of 2N HCl are then added and the crude acid precipitates. The aqueous phase is recovered and 300 ml of THF are added thereto. The mixture is dried over magnesium sulfate and the solvents evaporated. The resulting solid is taken up in 300 ml of hexane, filtered and oven dried at 100° C. under a vacuum, for 16 hours, yielding 1.16 g (98% yield) of the expected acid in the form of a gray-white powder which melts at 360° C.

EXAMPLE VI

Methyl ester of p-(7-tert.butyl-6-methoxy-2-naphthyl)-benzoic acid (a) Methyl ester of p-[1-(2,2-dimethoxyethyl)-2-(3-tert.butyl-4-methoxyphenyl)-vinyl]benzoic acid 5.49 g (28.56 mmoles) of 3-tert.butyl-4-methoxy-benzoic aldehyde are dissolved in 100 ml of THF. The solution is cooled to −78° C. and there is added thereto a solution of lithium di-isopropylamide-(34.55 mmoles) in THF (50 ml), prepared as indicated above. The reaction is carried out as in EXAMPLE IV(c). After extraction three times with 200 ml of ether and treatment as in EXAMPLE IV(b), 5.73 g (49% yield) of the mixture of the expected E and Z esters in the form of a yellow oil are obtained.

(b) Methyl ester of p-(7-tert.butyl-6-methoxy-2-naphthyl)-benzoic acid 5.67 g (13.74 mmoles) of the mixture of ester obtained in part (a) above are all dissolved in 400 ml of dichloromethane. 1 ml of TMSOTf is added and the mixture is irradiated with UV for 2 hours. The solvent is evaporated and the residue is chromatographed through a silica column (eluant: 60:40 mixture of CH$_2$Cl$_2$ and hexane), yielding 3.00 g (63% yield) of the methyl ester of p-(7-tert.butyl-6-methoxy-2-naphthyl) benzoic acid which melts at 133° C.

EXAMPLE VII p-(7-tert.butyl-6-methoxy-2-naphthyl) -benzoic acid

The ester obtained in Example VI(b) is dissolved in 60 ml of methanol. 6 ml of 5N NaOH are added and the mixture is heated at reflux for 1 hour. The methanol is then evaporated and 300 ml of water are added. This mixture is extracted five times with 100 ml of ether, dried over MgSO$_4$, filtered and evaporated under reduced pressure. The resulting solid is taken up in 100 ml of hexane, filtered and dried, yielding 0.92 g (96% yield) of the expected acid which melts at 283° C.

EXAMPLE VIII

Methyl ester of p-[7-(1-adamantyl)-6-hydroxy-2-naphthyl ]-benzoic acid (a) 2-[3-[3-(1-adamantyl)-4-tert.butyl-dimethylsilyloxyphenyl]-allyl ]-1, 3-dioxane 33 g (72.1 mmoles) of [2-(1,3-dioxan-2yl)ethyl ]triphenylphosphonium bromide are suspended in 100 ml of THF. The suspension is cooled to 0° C. and 8.5 g (75.6 moles) of potassium terbutylate are added in small amounts. The mixture is left to stand until it,s temperature reaches 20.° C. It is then stirred for 1 hour at which point it is cooled to 0° C. There is then slowly added a solution of 3(1-adamantyl)-4-tert.butyl-dimethylsilyloxybenzaldehyde in 100 ml of TMF. Once the addition has ended, the mixture is left to stand until its temperature reaches ambient temperature at which point it is stirred for 2 hours, then poured into water, and extracted with methylene chloride. The organic phase is decanted, washed with water, dried over MgSO$_4$ and the solvents evaporated. The residue is purified by passage through a silica column (eluant: 50:50 mixture of CH$_2$Cl$_2$ and hexane), yielding 19.4 g (95% yield) of the expected mixture containing more than 90% of isomer Z, and less than 10% of isomer E.

(b) Methyl ester of p-[1-[(1,3-dioxan-2-yl)methyl]-2-[3-(1-adamantyl)-4-tert.butyl-dimethylsilyloxyphenyl]-vinyl]-benzoic acid There are successively added in a round bottom flask: 19.1 g (40.8 mmoles) of the dioxane derivative prepared in part (a) above; 8.8 g of methyl p-bromobenzoate; 183 mg (0.8 mole) of palladium acetate; 428 mg. (1.6 mole) of triphenylphosphine; and 11.3 g (81.6 moles) of finely divided potassium carbonate. This mixture is heated under nitrogen at 180° C. for 2 hours. After cooling to ambient temperature, the resulting solid is treated with a mixture of dichloromethane and water. The organic phase is decanted, washed with water, dried over MgSO$_4$, filtered and the solvents evaporated. The resulting residue is chromatographed on a silica column (eluant: 80:20 mixture of CH$_2$Cl$_2$ and hexane) to give 9.5 g (39% yield) of the methyl ester of p-[1-[(1,3-dioxan-2-yl)-methyl]-2-[3-(1-adamantyl)-4-tert.butyl-dimethylsilyloxyphenyl]-vinyl]-benzoic acid.

(c) Methyl ester of p-[7-(1-adamantyl)-6-tert.butyl-dimethylsilyloxy-2-naphthyl]-benzoic acid 9.0 g (14.9 mmoles) of the ester obtained in part (b) above are dissolved in 400 ml of dichloromethane. 2 ml of TMSOTf are added and the mixture is stirred for 3 hours 30 minutes under nitrogen and under UV irradiation. After evaporation of the dischloromethane, the residue is deposited on a silica column and eluted with a 50:50 mixture of dichloromethane and hexane. After evaporation of the solvents, the resulting light yellow solid is stirred in 100 ml of cold hexane. On filtration 4.55 g (58% yield) of the expected ester in the form of a white powder melting at 185° C. are obtained.

(d) Methyl ester of p-[7-(1-adamantyl)-6-hydroxy-2-naphthyl]-benzoic acid 4.55 g (8.6 mmoles) of the ester obtained in part (c) above are dissolved in 30 ml of dry THF.

9.5 ml of a molar solution of tetrabutylammonium fluoride in THF are slowly added. The resulting orange colored solution is stirred for 2.5 hours at 20° C. The THF is evaporated. After adding water the mixture is extracted three times with 200 ml of ethylether. The organic phase is washed with a saturated solution of sodium chloride, dried over MgSO$_4$, then evaporated. 3.51 g (99% yield) of the expected ester in the form of a white-to-beige solid which melts at 247° C. are thus obtained.

EXAMPLE IX p-[7-(1-adamantyl)6-hydroxy-2-naphthyl]benzoic acid 1.24 g (3 mmoles) of the ester obtained in Example VIII(c) are suspended in 60 ml of methanol. 6 ml of 5N NaOH are added and the mixture is heated at reflux for 1 hour. The methanol is evaporated and 200 ml of 2N HCl are added. The mixture is then extracted three times with 400 ml of ethylether. The organic phase is washed initially with a saturated solution of sodium bicarbonate and then with NaCl, dried and evaporated. 1.08 g (90% yield) of the expected acid which melts at 295°–300° C. are obtained.

EXAMPLE X

Methyl ester of
5-(5,6,7,8-tetrahydro-5,5,8,8-tetramethyl-
2-anthracenyl)-2-furane carboxylic acid (a) 2-[3-(5,6,7,8-tetrahydro-5,5,8,8-tetramethyl-2-naphthyl)-allyl]-1,3-dioxane In a manner analogous to the procedures of Example VIII(a), strating with 25.2 g (55 mmoles) of [2-(1,3-dioxanyl2-yl] triphenylphosphonium bromide and 10.8 g (50 mmoles) of 5,6,7,8-tetrahydro-5,5,8,8-tetramethyl-2-naphthaldehyde, there are obtained, after chromatography on a silica column (eluant: hexane 95%, ether 5%), 4 g (66% yield) of 2-[3(5,6,7,8-tetrahydro-5,5,8,8-tetramethyl-2-naphthyl).allyl]-1,3-dioxane in the form of a yellow oil.

(b) Methyl ester of E-5-[1-[(1,3-dioxan-2-yl)methyl]-2-(5, 6,7,8-tetrahydro-5,5,8,8-tetramethyl-2-naphthyl)-vinyl]-2-furane carboxylic acid 9.42 g (30 mmoles) of the substituted dioxane derivative obtained above in part (a), 6.15 g (30 mmole) of methyl 5-bromo-2-furoate, 135 mg (0.6 mmole) of Pd (OAc)$_2$, 315 mg (1.2 mmole) of P (C$_6$H$_5$)$_3$ and 8.2 g (60 mmole) of finely divided potassium carbonate are heated at 160° C. for 2 hours. 3.07 g (15 mmoles) of methyl bromofuroate, 135 mg of Pd(OAc)$_2$ and 315 mg of P(C$_6$H$_5$)$_3$ are then added thereto. Beating is continued for an additional 2 hours. The reaction mixture is then cooled and purified by passage through a silica column (eluant: 80/20 mixture of dichloromethane and hexane), yielding 7.1 g (53% yield) of the expected ester which melts at 123°–124° C.

(c) Methyl ester of 5-(5,6,7,8-tetrahydro-5,5,8,8-tetramethyl-2-anthracenyl)-2-furane carboxylic acid 7 g (16 mmoles) of the ester obtained in part (b) above are dissolved in 200 ml of dichloromethane. This solution is cooled to 0° C. and 1 ml of TMSOTf is added thereto. The mixture is left to stand until the temperature returns to ambient temperature at which point the mixture is stirred for 30 minutes. The solvent is evaporated and the residue is purified by passage through a silica column (eluant: 50/50 mixture of dichloromethane and hexane). The resulting product can be recrystallized in hexane to give 5.5 g (96% yield) of the expected ester which melts at 127° C.

EXAMPLE XI 5-(5,6,7,8-tetrahydro-5,5,8,8-tetramethyl-
2-anthracenyl)-2-furane carboxylic acid 5.2 g (14 moles) of the ester obtained in Example X(c) are treated for 4 hours at reflux with 200 ml of 2N methanolic NaOH. The reaction mixture is then evaporated and the residue is taken up in water, acidified with concentrated HCl, extracted with ether, washed with water, dried over MgSO$_4$, evaporated and recrystallized in a 50:50 mixture of isopropyl ether and ethyl acetate. There are thus obtained 4.6 g (93% yield) of 5-(5,6,7,8-tetrahydro-5,5,8,8-tetramethyl-2-anthracenyl)-2-furane carboxylic acid which melts at 229°–230° C.

EXAMPLE XII

Methyl ester of
5-(5,6,7,8-tetrahydro-5,5,8,8-tetramethyl-
2-anthracenyl)-2-thiophene carboxylic acid (a) Methyl ester of 5-[1-[(1,3-dioxan-2-yl)methyl]-2-(5, 6,7,8-tetrahydro-5,5,8,8-tetramethyl-2-naphthyl) -vinyl]-2-thiophene carboxylic acid In a round bottom flask there are introduced: 9.42 g (30 mmoles) of the dioxane derivative obtained in Example X(a), 6.63 g (30 mmoles) of methyl 5-bromo-2-thiophenecarboxylate, 135 mg of Pd(OAc)$_2$, 315 mg (1.2 mmole) of P(C$_6$H$_5$)$_3$ and 8.3 g (60 mmoles) of finely divided K$_2$CO$_3$. The mixture is heated under nitrogen at 200° C. for 2 hours. 3.3 g (15 mmoles) of methyl 5-bromothiophene-carboxylate are then added and the mixture is heated again for 2 hours.

The reaction mixture is imperfectly purified on a silica column (eluant: 80:20 mixture of dichloromethane and hexane) to obtain 5.4 g of a non-separable mixture under the conditions employed, of the expected product (60%) and E-2[3-(5,6,7,8-tetramethyl-5,5,8,8-tetramethyl)-2-naphthyl]-allyl-1,3-dioxane (40%). This mixture is used as such in the continuation of the synthesis.

(b) Methyl ester of 5-(5,6,7,8-tetrahydro-5,5,8,8-tetramethyl-2-anthracenyl)-2-thiophene carboxylic acid The mixture obtained in part (a) above, (5.2 g) is dissolved in 100 ml of dichloromethane. The resulting solution is cooled to 0° C. and 500 μl of TMSOTf are added thereto. The reaction mixture is left to stand until its temperature reaches 20° C. at which point it is stirred for 30 minutes. The solvent is evaporated and the resulting residue is purified by passage through a silica column (eluant: 50–50 mixutre of CH$_2$Cl$_2$ and hexane). The resulting product can be recrystallized in cyclohexane to give 2.5 g of the methyl ester of 5-(5,6,7,8-tetrahydro-5,5,8,8-tetramethyl-2-anthracenyl)-2-thiophene carboxylic acid which melts at 147°–148° C.

EXAMPLE XIII

5-(5,6,7,8-tetrahydro-5,5,8,8-tetramethyl-anthracenyl)-2-thiophene carboxylic acid 2.1 g (5.5 moles) of the ester obtained in Example XII(b), are treated at reflux for 8 hours with 100 ml of 2N methanolic NaOH. The methanol is evaporated and the residue is taken up in water, acidified with concentrated HCl, extracted with ether, dried over $MgSO_4$ and evaporated. The residue is recrystallized in a 60:40 mixture of isopropyl ether and ethyl acetate, yielding 5 g (90% yield) of 5-(5,6,7,8-tetrahydro-5,5,8,8-tetramethyl-2-anthracenyl)-2-thiophene carboxylic acid which melts at 254°–255° C.

EXAMPLE XIV

Methyl ester of p-[3,4(2H)-dihydro-4,4-dimethyl-7-naphtho-[2,3-b]pyranyl]-benzoic acid (a) Methyl ester of p-[1-(2,2-dimethoxyethyl)-2-(4,4-dimethyl-6-chromanyl)-vinyl]benzoic acid In a manner analogous to the procedures of EXAMPLE IV, 6.49 g (17.3 moles) of phosphonate, prepared in EXAMPLE II(b), dissolved in THF (20ml) are treated with a solution of lithium diisopropylamide (17.3 moles) in THF (20 ml). A solution of 6-formylchromane is added and the resulting mixture is stirred for 2 hours at −78° C. The reaction mixture is then left to stand until its temperature reaches ambient temperature, at which point it is poured into water and extracted with ether. The organic phase is dried over $MgSO_4$, and the solvents are evaporated. The resulting residue is chromatographed on a silica Column (eluant: hexane) yielding 950 mg (15% yield) of the E, Z mixture of the methyl esters of p [[1-(2,2dimethoxyethyl)-2-(4,4-dimethyl-6-chromanyl)]-vinyl]benzoic acid in the form of a pale yellow oil which is used as such in the continuation of the synthesis.

(b) Methyl ester of p-[3,4(2H)-dihydro-4,4-dimethyl-7-naphtho 2,3-b)-pyranyl]benzoic acid 950 g (2.3 mmoles) of the E+Z mixture of esters obtained above in part (a) are dissolved in 200 ml of dichloromethane. 0.5 ml of TMSOTf is added and the mixture is irradiated with UV, under nitrogen, while stirring. At the end of 3 hours, the solvents are evaporated. The resulting residue is chromatographed on a silica column (4×25 cm, eluant-50:50 mixture of dichloromethane and hexane). On evaporation, 430 mg (54% yield) of the methyl ester of p-[3,4(2H)-dihydro-4,4-dimethyl-7naphtho[2,3-b]pyranyl]-benzoic acid which melts at 153°–154° C. are obtained.

EXAMPLE XV p-[3,4(2H-dihydro-4,4-dimethyl-7-naphtho 2,3,-b] pyranyl ]-benzoic acid 370 mg (1.06 mmoles) of the ester obtained in Example XIV(b) are suspended in 40 ml of methanol. 400 mg of NaOH pellets are added and the mixture is heated at reflux for 2 hours while stirring. The methanol is evaporated and 300 ml of water are added. After neutralization with 1N HCl, the reaction mixture is extracted with ether (3×300 ml). The organic phase is washed with water saturated with NaCl, dried over $MgSO_4$ and the solvent are evaporated, yielding 240 mg (68% yield) of p-[3,4(2H)-dihydro-4,4-dimethyl-7-naphtho[2,3,-b]pyronyl]benzoic acid which melts at 249°–250° C.

EXAMPLE XVI

Ethylamide of 5-(5,6,7,8-tetrahydro-5,5,8,8-tetramethyl-2-anthracenyl)-2-furane carboxylic acid (a) Chloride of 5-(5,6,7,8-tetrahydro-5,5,8,8-tetramethyl-2-anthracenyl)-2-furane carboxylic acid 1.15 g (3.31 mmoles) of the acid obtained in Example XI are treated with 5 ml of thionyl chloride at 40° C. for 1 hour. The reaction mixture is evaporated to dryness and the residue is taken up in bezene and re-evaporated, yielding 1.17 g of a highly crystalline mass that one uses as such in the continuation of the synthesis.

(b) Ethylamide of 5-(5,6,7,8-tetrahydro-5,5,8,8-tetramethyl-2-anthracenyl)-2-furane carboxylic acid 200mg (0.54 mole) of the chloride of the acid obtained above in part (a) dissolved in 20 ml of dry $CH_2Cl_2$ are added to a solution of ethylamine (184 mg; 4.08 moles) in 1 ml of $CH_2Cl_2$. The mixture is stirred at ambient temperature for 15 minutes. Water is added and the mixture is acidified to pH 1 with 1N HCl, extracted with $CH_2Cl_2$, washed initially with a saturated solution of $NaHCO_3$, then with water, dried, the solvents evaporated. 110 mg (54% yield) of the expected amide which melts at 200° C. are obtained.

EXAMPLE XVII

Morpholide of 5-(5,6,7,8-tetrahydro-5,5,8,8-tetramethyl-2-anthracenyl)-2-furane carboxylic acid To 200 mg (0.54 mmole) of the chloride of the acid obtained in Example XVI(a) dissolved in 20 ml of $CH_2Cl_2$ are added 237 mg (2.72 mmoles) of morpholine. The mixture is stirred for 15 minutes at which point water is added. The mixture is then acidified to pH 1 with 1N HCl and the organic phase is recovered. This organic phase is initially washed with a saturated solution of $NaHCO_3$ and then with water, dried over $MgSO_4$ and evaporated. The resulting residue is purified by passage through a silica column (eluant: 95/5 mixture of $CH_2Cl_2$ and acetone). On evaporation of the solvents 193 mg (85% yield) of the morpholide of 5-(5,6,7,8-tetrahydro-5,5,8,8-tetramethyl-2-anthracenyl)-2-furane carboxylic acid which melts at 161° C. are obtained.

EXAMPLE XVIII

2-hydroxyethyl 5-(5,6,7,8-tetrahydro-5,5,8,8-tetramethyl-2-anthracenyl)-2-furane carboxylate 340 mg (5.4 mmoles) of ethyleneglycol are dissolved in 1 ml of $CH_2Cl_2$. To this solution there are added 86 mg (1.1 mmole) of pyridine and 200 mg (0.54 mole) of the chloride of the acid obtained in EXAMPLE XVI(a), dissolved in 20 ml of $CH_2Cl_2$. This mixture is stirred at ambient temperature for 15 minutes at which point water is added. The resulting mixture is acidified to pH1 with 1N HCl, extracted with dichloromethane, washed,successively with a saturated solution of sodium bicarbonate, then with water, dried over $MgSO_4$ and evaporated. The resulting residue is passed through a silica column (eluant - 95/5 mixture of $CH_2Cl_2$ and acetone). On evaporation of the solvents 152 mg (71% yield) of the expected ester which melts at 143° C. are obtained.

EXAMPLE XIX p-(5,6,7,8-tetrahydro-5,5,8,8-tetramethyl-2-anthracenyl) benzyl alcohol 300 mg (0.83 mmole) of p-(5,6,7,8-tetrahydro-5,5,8,8-tetramethyl-2-anthracenyl) benzoic acid obtained in EXAMPLE III above are dissolved in THF. 48 mg (1.25 mmoles) of $LiAlH_4$ are added and the mixture is stirred initially for 15 minutes at ambient temperature and then for 10 minutes at reflux. The mixture is then left to stand until its temperature returns to ambient temperature. 28 µl of a saturated solution of sodium and potassium tartrate are then added. The mixture is then filtered and the THF is evaporated. The resulting residue is taken up in hexane and the precipitate that forms is filtered, yielding 167 mg (57% yield) of the expected alcohol which melts at 131° C.

EXAMPLE XX 2-(4-methylphenyl)-5,6,7,8-tetrahydro-5,5,8,8-tetramethylanthracene.

(a) E-2-[-2-(4-methylphenyl)-3-(5,6,7,8tetrahydro-5,5,8,8-tetramethyl-2-naphthyl) allyl]1,3-dioxane.

1.5 g (5mmoles) of 2-[3-(5,6,7,8-tetrahydro-5,5,8,8-tetramethyl-2-naphthyl)-allyl]-1,3-dioxane, 850mg (5 mmoles) of 4bromotoluene, 25mg (0.1 mmole) of Pd $(OAc)_2$ 55 mg (0.2mmole)of P $(C_6H_5)_3$ and 1.4 g (10 mmoles) of potassium carbonate are heated at 180° C. for 2 hours under passage of nitrogen.

The reaction mixture is then cooled and purified by passage over a silica column eluting with a 50–50 mixture of dichloromethane and hexane. By this means, 520mg (24%) of the expected product is obtained as a slightly yellowed oil.

(b) 2-(4-methyl phenyl)-5,6,7,8-tetrahydro-5,5,8,8-tetramethylanthracene 480 mg (1.1 mmole) of the derivative above are dissolved in 20 ml of dichloromethane. On cooling to 0° C., 100 µl of the trimethylsilyl ester of trifluoromethane sulfonic acid are added while stirring for 30 minutes at ambient temperature. Next the reaction medium is poured into water, extracted with ethyl ether, the organic phase decanted followed by drying on magnesium sulphate before evaporating. The resulting residue is purified by silica column chromatography using a 95–5 hexane-dichloromethane mixture as eluant. Evaporation of the solvents yields 310mg (80%) of 2-(4-methylphenyl)-5,6,7,8-tetrahydro-5,5,8,8-tetramethylanthracene which melts at 91°–2° C.

EXAMPLES OF COMPOSITIONS

A-Orally Administrable Compositions

Example 1

0.29 Tablet

| | |
|---|---|
| p-(5,6,7,8-tetrahydro-5,5,8,8-tetramethyl-2-anthracenyl) benzoic acid | 1 µg |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

In this example the active compound can be replaced by the same amount of the methyl ester of 5-(5,6,7,8-tetrahydro-5,5,8,8-tetramethyl-2-anthracenyl)-2-thiophene carboxylic acid.

Example 2

0.49 capsule containing a suspension

| | |
|---|---|
| p-(6-tert.butyl-2-naphthyl) benzoic acid | 0.001 g |
| Glycerine | 0.200 g |
| Sucrose | 0.050 g |
| Polyethylene glycol 400 | 0.050 g |
| Purified water, sufficient amount for | 0.400 g |

This suspension is packaged in a capsule made of gelatin, glycerins, titanium dioxide and water.

In this example the active compound can be replaced by the same amount of the methyl ester of p-(7-tert.butyl-6-methoxy-2-naphthyl) benzoic acid.

B-Topically Administratable Compositions

Example 1

Ointment

| | |
|---|---|
| p-(5,6,7,8-tetrahydro-5,5,8,8-tetramethyl-2-anthracenyl) benzoic acid | 0.0001 g |
| Stearyl alcohol | 3.000 g |
| Lanolin | 5.000 g |
| Petrolatum | 15.000 g |
| Distilled water, sufficient amount for | 100.000 g |

In this example the active compound can be replaced by the same amount of the ethyl ester of p-(5,6,7,8-tetrahydro-5,5,8,8-tetramethyl-2anthracenyl)-benzoic acid.

Example 2

Gel

| | |
|---|---|
| Ethyl ester of p-(5,6,7,8-tetrahydro-5,5,8,8-tetramethyl-2-anthracenyl) benzoic acid | 0.005 g |
| Hydroxypropylcellulose, sold by Hercules under the trade designated "KLUCEL HF" | 2.000 g |
| water/ethanol (50:50) sufficient amount for | 100.000 g |

In this example the active compound can be replaced by 0.00059 of p-(7-tert.butyl-6-methoxy-2naphthyl) benzoic acid.

Example 3

Oil-in-water non-ionic cream

| | |
|---|---|
| 2-hydroxyethyl 5-(5,6,7,8-tetrahydro-5,5,8,8-tetramethyl-2-anthracenyl)-2-furane carboxylate | 0.001 g |
| Cetyl alcohol | 3.00 g |
| Stearyl alcohol | 3.400 g |
| Cetyl alcohol oxyethylenated with | 0.630 g |

23
-continued

| | |
|---|---|
| 20 moles of ehylene oxide | |
| Stearyl alcohol oxyethylenated with 20 moles of ethylene oxide | 1.470 g |
| Glycerol monostearate | 2.000 g |
| Petrolatum oil | 15.000 g |
| Glycerine | 10.000 g |
| Preservative | 0.050 g |
| Distilled water, sufficient amount for | 100.000 g |

Example 4

Oil-in-water anionic cream

| | |
|---|---|
| Ethylamide of 5-(5,6,7,8-tetrahydro-5,5,8,8-tetra methyl-2-anthracenyl)-2-furane carboxylic acid | 0.002 g |
| Sodium dodecyl sulfate | 0.800 g |
| Glycerol | 2.000 g |
| Stearyl alcohol | 20.000 g |
| Triglycerides of capric/caprylic acid sold by Dynamit Nobel under the name "MIGLYOL 812" | 20.000 g |
| Preservative | 0.050 g |
| Demineralized water, sufficient amount for | 100.000 g |

C - Cosmetic Compositions

Example 1

Anhydrous lotion

| | |
|---|---|
| Methyl ester of p-[7-(1-adamantyl)-6-methoxy-2-naphthyl] benzoic acid | 0.001 g |
| Absolute ethanol | 30. g |
| Polyethylene glycol, sufficient amount for | 100 g |

Example 2

Anhydrous gel

| | |
|---|---|
| p-[7-(1-adamantyl)-6-methoxy-2-naphthyl] benzoic acid | 0.001 g |
| Monoethylester of diethylene glycol | 35 g |
| Hydroxypropyl cellulose | 1 g |
| Preservatives, sufficient amount | |
| Polyethylene glycol, sufficient amount for | 100 g |

Example 3

Bath Oil

| | |
|---|---|
| Methyl ester of p-[7-(1-adamantyl)-6-methoxy-2-naphthyl] benzoic acid | 0.001 g |
| Ethoxylated fatty alcohol | 10.00 g |
| Octyldodecanol | 20.00 g |
| Isopropyl mysistate | 25.00 g |
| Essential oil | 5.00 g |
| Triglycerides of $C_8$–$C_{10}$ acid, sufficient amount for | 100.00 g |

24

Example 4

Non-soluble Stick

| | |
|---|---|
| p-[7-(1-adamantyl)-6-methoxy-2-naphthyl] benzoic acid | 0.001 g |
| Cocoa butter | 12.50 g |
| Ozokerite wax | 18.50 g |
| Hard paraffin (drop point: 58° C.) | 6.25 g |
| White petrolatum | 12.75 g |
| Isopropyl myristate, sufficient amount for | 100.00 g |

Example 5

Shampoo gel

| | |
|---|---|
| 5-(5,6,7,8-tetrahydro-5,5,8,8-tetramethyl-2-anthracenyl)-2-furane carboxylate of 2-hydroxyethyl | 0.002 g |
| Sodium lauryl sulfate | 50.00 g |
| Cocobetaine | 20.00 g |
| Preservatives, sufficient amount | 100.00 g |
| Coloring agent, sufficient amount | |
| Perfume, sufficient amount | |
| Water, sufficient amount for | |

Example 6

Moderately viscous shampoo

| | |
|---|---|
| 5-(5,6,7,8-tetrahydro-5,5,8,8-tetramethyl-2-anthracenyl)-2-furane carboxylate of 2-hydroxy ethyl | 0.002 g |
| Sodium lauryl ether sulfate | 40. g |
| Diethanolamide of copra fatty acid | 3.00 g |
| Sodium chloride | 2.00 g |
| Preservatives, sufficient amount | 100.00 g |
| Coloring agent, sufficient amount | |
| Perfume, sufficient amount | |
| Water, sufficient amount for | |

What is claimed is:

1. A polycyclic aromatic compound having the formula

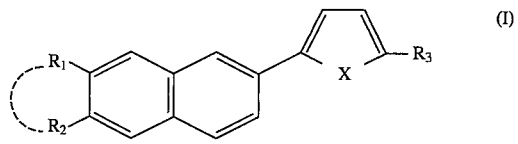

(I)

wherein

X represents O or S, $R_1$ represents hydrogen, branched alkyl having 3–15 carbon atoms, alkoxy having 1–6 carbon atoms or 1-adamantyl, $R_2$ represents hydrogen, hydroxy, linear or branched alkyl having 1–15 carbon atoms or alkoxy having 1–6 carbon atoms, with the proviso that $R_1$ and $R_2$ are not simultaneously hydrogen, or $R_1$ and $R_2$ together with the adjacent carbon atoms of the naphthalene ring form a 5 or 6 carbon ring optionally substituted by at least one lower alkyl radical, or interrupted by an oxygen atom, $R_3$ represents —$CH_2OH$ or —$COR_4$ or $R_3$ represents —$CH_3$ when $R_1$ and $R_2$ taken together form a 5 or 6 carbon ring, R₄ represents

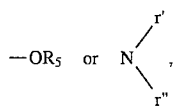

R₅ represents hydrogen, alkyl having 1–20 carbon atoms, monohydroxyalkyl, polyhydroxyalkyl, aryl or aralkyl optionally substituted, or the residue of a sugar or the radical

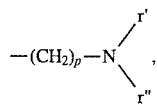

p is 1, 2 or 3, r' and r" represent hydrogen, lower alkyl, monohydroxyalkyl, polyhydroxyalkyl, aryl optionally substituted as the residue of an amino acid or the residue of an amino sugar, or taken together form a heterocycle, and the salts of said polycyclic aromatic compound of formula I.

2. The compound of claim 1 wherein said alkyl having 1–20 carbon atoms is methyl, ethyl, propyl, 2-ethylhexyl, octyl, dodecyl, hexadecyl or octadecyl.

3. The compound of claim 1 wherein said monohydroxyalkyl is 2-hydroxyethyl or 2-hydroxypropyl.

4. The compound of claim 1 wherein said polyhydroxyalkyl is 2,3-dihydroxypropyl, 2,3,4-trihydroxybutyl, 2,3,4,5-tetrahydroxypentyl or the residue of pentaerythritol.

5. The compound of claim 1 wherein said residue of a sugar is a residue derived from glucose, mannose, erythrose or galactose.

6. The compound of claim 1 wherein said residue of an amino sugar is a residue derived from glucosamine, galactosamine or mannosamine.

7. The compound of claim 1 wherein r' and r" taken together form a heterocycle selected from the group consisting of piperidino, piperazino, morpholino and pyrrolidino.

8. The compound of claim 1 selected from the group consisting of 5-(5,6,7,8-tetrahydro-5,5,8,8-tetramethyl-2-anthracenyl)-2-furane carboxylic acid, the methyl ester of 5-(5,6,7,8-tetrahydro-5,5,8,8-tetramethyl-2-anthracenyl)-2-furane carboxylic acid, 5-(5,6,7,8-tetrahydro-5,5,8,8-tetramethyl-2-anthracenyl)-2-thiophene carboxylic acid, the methyl ester of 5-(5,6,7,8-tetrahydro-5,5,8,8-tetramethyl-2-anthracenyl)-2-thiophene carboxylic acid, the ethylamide of 5-(5,6,7,8-tetrahydro-5,5,8,8-tetramethyl-2-anthracenyl)-2-furane carboxylic acid and 2-hydroxyethyl-5-(5,6,7,8-tetrahydro-5,5,8,8-tetramethyl-2-anthracenyl)-2-furane carboxylate.

9. The compound of claim 1 having the formula

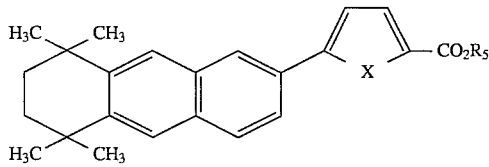

wherein

X is O or S and

R₅ represents hydrogen or alkyl.

10. A process for preparing a compound having the formula

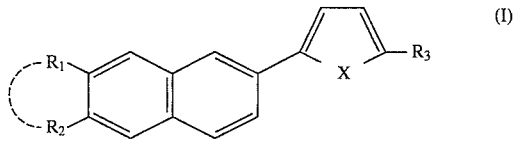

wherein

X represents —CH=CH—, O or S,

R₁ represents hydrogen, branched alkyl having 3–15 carbon atoms, alkoxy having 1–6 carbon atoms or 1-adamantyl, R₂ represents hydrogen, hydroxy, linear or branched alkyl having 1–15 carbon atoms or alkoxy having 1–6 carbon atoms, with the proviso that R₁ and R₂ are not simultaneously hydrogen, or R₁ and R₂ together with the adjacent carbon atoms of the naphthalene ring form a 5 or 6 carbon ring optionally substituted by at least one lower alkyl radical, or interrupted by an oxygen atom, R₃ represents —CH₂OH or —COR₄ or R₃ represents —CH₃ when R₁ and R₂ taken together form a 5 or 6 carbon ring, R₄ represents —OR₅ or

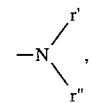

represents hydrogen, alkyl having 1–20 carbon atoms, monohydroxyalkyl, polyhydroxyalkyl, aryl or aralkyl optionally substituted, or the residue of a sugar or the radical

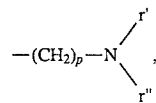

p is 1, 2 or 3, r' and r" represent hydrogen, lower alkyl, monohydroxyalkyl, polyhydroxyalkyl, aryl optionally substituted as the residue of an amino acid or the residue of an amino sugar, or taken together form a heterocycle, said process comprising (1) reacting by a coupling reaction of the Wittig or Wittig-Horner type an aromatic aldehyde having the formula

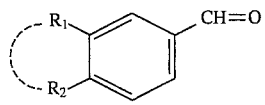

wherein

R₁ and R₂ have the same meanings given above, with a pentavalent phosphorous derivative having the formula

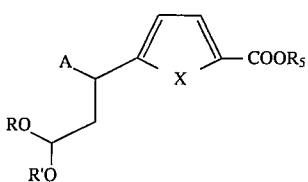

wherein

X and $R_5$ have the same meanings given above,

A represents (i)—$P[X']_3^+Y^-$ wherein X' represents aryl and Y represents an anion of an organic or inorganic acid, or (ii)

wherein Z represents alkoxy, and R and R' represent lower alkyl or taken together form a dioxane or dioxolane ring, and (2) effecting a cyclization-aromatization reaction of the product obtained in step (1), in a chlorinated solvent, in the presence of an acid catalyst, said reaction optionally being effected under UV radiation.

11. The process of claim 10 wherein A represents

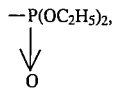

said coupling reaction in step (1) being carried out in the presence of lithium di-isopropylamide in tetrahydrofuran at a temperature of about −80° C.

12. The process of claim 10 wherein said cyclization-aromatization reaction of step (2) is carried out in dichloromethane or chloroform in the presence of sulfuric acid, paratoluene sulfonic acid or trifluoromethane sulfonate of trimethylsilyl.

13. A process for preparing a compound having the formula

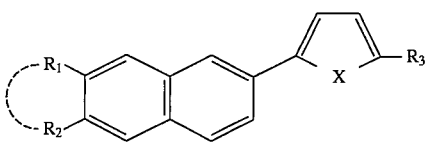

wherein

X represents —CH=CH—, O or S, $R_1$ represents hydrogen, branched alkyl having 3–15 carbon atoms, alkoxy having 1–6 carbon atoms or 1-adamantyl, $R_2$ represents hydrogen, hydroxy, linear or branched alkyl having 1–15 carbon atoms or alkoxy having 1–6 carbon atoms, with the proviso that $R_1$ and $R_2$ are not simultaneously hydrogen, or $R_1$ and $R_2$ together with the adjacent carbon atoms of the naphthalene ring form a 5 or 6 carbon ring optionally substituted by at least one lower alkyl radical, or interrupted by an oxygen atom, $R_3$ represented —$CH_2OH$ or —$COR_4$ or $R_3$ represents —$CH_3$ when $R_1$ and $R_2$ taken together form a 5 or 6 carbon ring, $R_4$ represents —$OR_5$ or

$R_5$ represents hydrogen, alkyl having 1–20 carbon atoms, monohydroxyalkyl, polyhydroxyalkyl, aryl or aralkyl optionally substituted, or the residue of a sugar or the radical

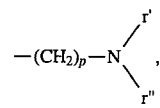

p is 1, 2 or 3, r' and r" present hydrogen, lower alkyl, monohydroxyalkyl, polyhydroxyalkyl, aryl optionally substituted as the residue of an amino acid or the residue of an amino sugar, or taken together form a heterocycle, said process comprising (1) reacting by a reaction of the Wittig or Wittig-Horner type an aromatic aldehyde of the formula

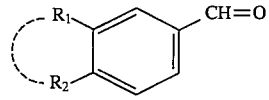

with a pentavalent phosphorus derivative of the formula

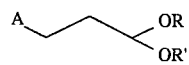

wherein $R_1$ and $R_2$ have the meanings given above,

A represents (i) —$P[X']_3^+Y^-$ wherein X' represents aryl and Y represents an anion of an organic or inorganic acid, or (ii)

wherein Z represents alkoxy, and

R and R' represent lower alkyl or taken together form a dioxane or dioxolane ring, (2) reacting the intermediate compound resulting from step (1), said intermediate compound having the formula

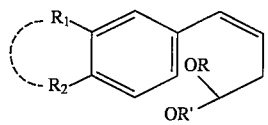

with a halogen-ester of the formula

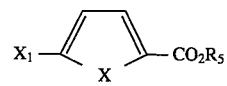

wherein

X and $R_5$ have the meanings given above and $X_1$ represents Cl and Br, and (3) effecting a cyclization-aromatization reaction of the product obtained in step (2).

14. A pharmaceutical composition comprising in a pharmaceutically acceptable vehicle at least one polycyclic aromatic compound having the formula

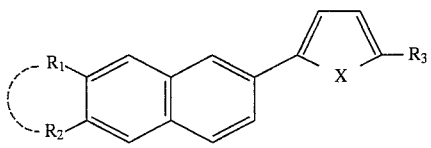 (I)

wherein

X represents —CH=CH—, O or S, $R_1$ represents hydrogen, branched alkyl having 3–15 carbon atoms, alkoxy having 1–6 carbon atoms or 1-adamantyl, $R_2$ represents hydrogen, hydroxy, linear or branched alkyl having 1–15 carbon atoms or alkoxy having 1–6 carbon atoms, with the proviso that $R_1$ and $R_2$ are not simultaneously hydrogen, or $R_1$ and $R_2$ together with the adjacent carbon atoms of the naphthalene ring form a 5 or 6 carbon ring optionally substituted by at least one lower alkyl radical, or interrupted by an oxygen atom, $R_3$ represents —CH$_2$OH or —COR$_4$ or $R_3$ represents —CH$_3$ when $R_1$ and $R_2$ taken together form a 5 or 6 carbon ring, $R_4$ represents —OR$_5$ or

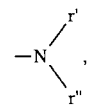

$R_5$ represents hydrogen, alkyl having 1–20 carbon atoms, monohydroxyalkyl, polyhydroxyalkyl, aryl or aralkyl optionally substituted, or the residue of a sugar or the radical

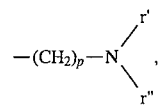

p is 1, 2 or 3, r' and r" represent hydrogen, lower alkyl, monohydroxyalkyl, polyhydroxyalkyl, aryl optionally substituted as the residue of an amino acid or the residue of an amino sugar, or taken together form a heterocycle, and the salts of said polycyclic aromatic derivative of Formula I.

15. The pharmaceutical composition of claim 14 wherein said polycyclic aromatic compound is present in an amount ranging from 0.00001 to about 5 percent by weight based on the total weight of said composition.

* * * * *